(12) United States Patent
Jung et al.

(10) Patent No.: US 7,886,776 B2
(45) Date of Patent: Feb. 15, 2011

(54) BANDAGE WITH LENGTHWISE ELASTICITY IN WARP DIRECTION

(75) Inventors: Harald Jung, Kreimbach-Kaulbach (DE); Frauke Haensch, Karlsruhe (DE); Karlheinz Szombach, Lauterecken (DE)

(73) Assignee: Karl Otto Braun GmbH & Co. KG, Wolfstein (DE)

( * ) Notice: Subject to any disclaimer, the term of this patent is extended or adjusted under 35 U.S.C. 154(b) by 259 days.

(21) Appl. No.: 11/988,086

(22) PCT Filed: Jul. 8, 2006

(86) PCT No.: PCT/EP2006/006714

§ 371 (c)(1), (2), (4) Date: Dec. 31, 2007

(87) PCT Pub. No.: WO2007/009625

PCT Pub. Date: Jan. 25, 2007

(65) Prior Publication Data

US 2009/0099497 A1   Apr. 16, 2009

(30) Foreign Application Priority Data

Jul. 15, 2005   (DE) .................. 10 2005 033 720

(51) Int. Cl.
*D03D 15/08* (2006.01)
*D03D 19/00* (2006.01)
*D03D 25/00* (2006.01)

(52) U.S. Cl. ................. 139/421; 139/422; 139/383 R; 139/420 A; 139/426 R

(58) Field of Classification Search ........... 139/383 R, 139/421, 422, 426 R, 420 A
See application file for complete search history.

(56) References Cited

U.S. PATENT DOCUMENTS

| | | | | |
|---|---|---|---|---|
| 1,035,107 A | | 8/1912 | Teufel | |
| 2,254,830 A | * | 9/1941 | Schloss | 4/582 |
| 2,387,320 A | * | 10/1945 | Foster | 57/211 |
| 2,544,223 A | * | 3/1951 | Ellis | 139/389 |
| 2,810,184 A | * | 10/1957 | Sherman | 28/156 |
| 3,013,379 A | * | 12/1961 | Breen | 57/6 |
| 3,154,111 A | * | 10/1964 | Marshall | 139/420 R |
| 3,409,008 A | * | 11/1968 | Mortensen et al. | 602/76 |
| 3,788,366 A | * | 1/1974 | Campbell et al. | 139/421 |
| 3,842,437 A | * | 10/1974 | Campbell et al. | 2/237 |
| 3,842,438 A | * | 10/1974 | Campbell et al. | 2/237 |
| 3,908,711 A | * | 9/1975 | Goff et al. | 139/419 |
| 3,965,943 A | * | 6/1976 | Goff et al. | 139/421 |
| 3,965,944 A | * | 6/1976 | Goff et al. | 139/421 |
| 4,207,885 A | | 6/1980 | Hampton | |
| 2001/0002493 A1 | * | 6/2001 | Wheeler et al. | 2/236 |

FOREIGN PATENT DOCUMENTS

| | | |
|---|---|---|
| AT | 154 588 | 10/1938 |
| DE | 490 705 | 1/1930 |
| DE | 11 64 021 | 2/1964 |
| DE | 22 40 945 | 2/1974 |
| DE | 85 28 007 | 1/1986 |
| DE | 100 33 210 | 1/2002 |
| EP | 1122346 * | 8/2001 |

* cited by examiner

*Primary Examiner*—Bobby H Muromoto, Jr.
(74) *Attorney, Agent, or Firm*—Paul Vincent

(57) ABSTRACT

A bandage with lengthwise elasticity in the warp direction, comprising a textile expanse woven in leno weave and having weft threads, leno threads and elastically extensible warp threads. The warp threads are cotton-elastic threads.

8 Claims, 2 Drawing Sheets a)

b)

c)

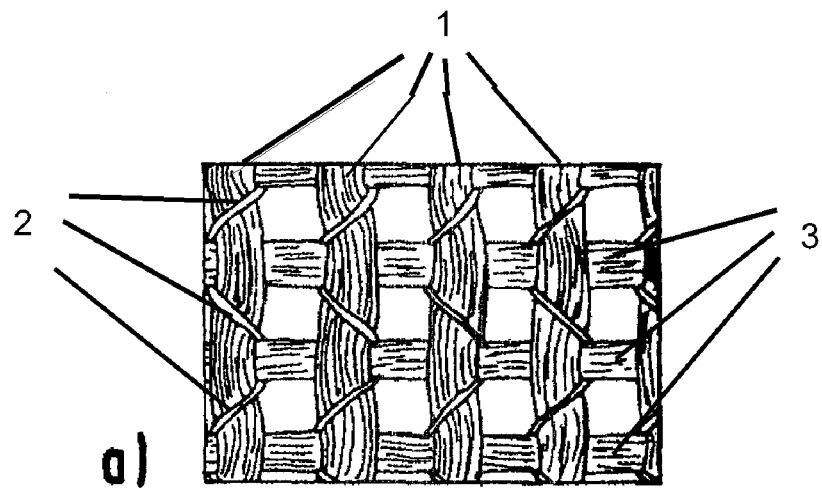
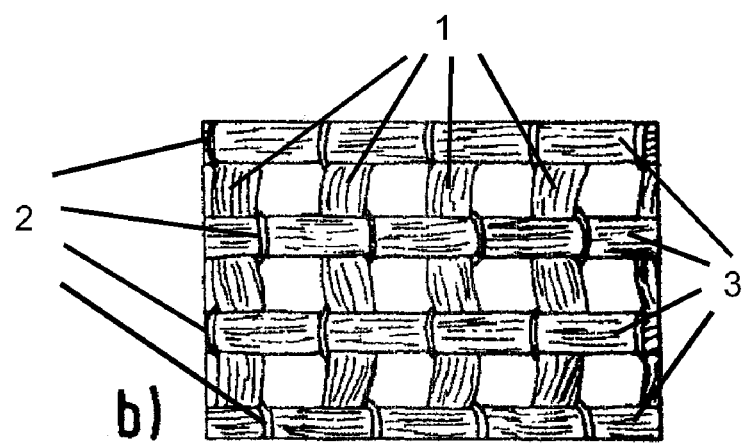
Fig. 1
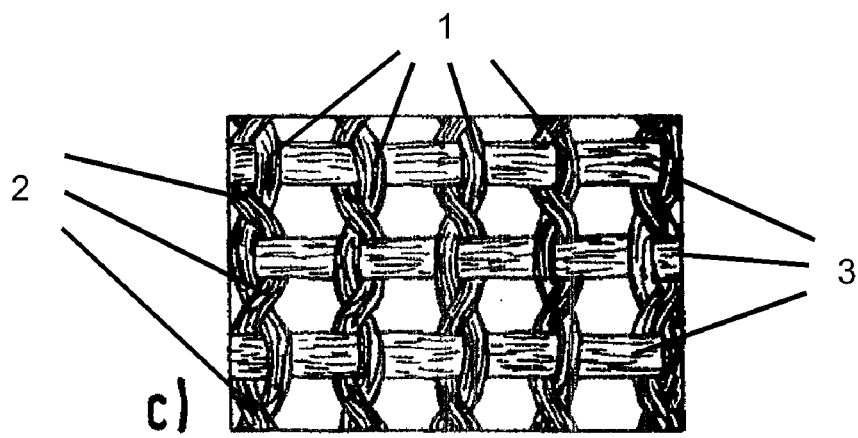

BANDAGE WITH LENGTHWISE ELASTICITY IN WARP DIRECTION

This is the national stage of PCT/EP2006/006714 filed on Jul. 8, 2006 and also claims Paris Convention priority of DE 10 2005 033 720.1 filed on Jul. 15, 2005.

BACKGROUND OF THE INVENTION

The invention relates to a bandage with lengthwise elasticity in the warp direction, with weft threads, leno threads and elastically extensible warp threads, the bandage being woven in leno weave, i.e. the warp threads and weft threads being interwoven by leno threads. This is a leno fabric of the "half-cross leno" type. Such half-cross leno types include mesh fabrics having only one warp thread and one leno thread per group. Leno fabrics have the principal advantage of having high slip resistance. The slip resistance of a fabric is determined by the frictional forces between the individual threads.

DE 100 33 210 A1, for example, discloses use of a textile carrier which is coated with a hardenable reaction resin (moisture curing plastic) and/or impregnated for the production of a support bandage, the carrier material of which can be manufactured in the leno weaving procedure. Such materials are used for the production of so-called "cast bandages", the plastic material then hardening completely for formation of a rigid or semi-rigid support bandage. In this case, a permanent elasticity of such a bandage material is not required.

Moreover, an elastic compression bandage is known from U.S. Pat. No. 4,207,885, for example, in which individual warp threads can bind in leno weave in order to improve the slip resistance of the fabric.

The bandage consists of an elastic nylon fabric. Nevertheless, although having good elastic properties, such synthetic fibers are not comfortable enough for the patients with respect to the wearing properties. Under the aspect of the patient's comfort, it is particularly preferred when the respective bandages are made of natural fibers. Moreover, such bandages create comparatively high restoring forces even at slight elongation (resting pressure).

Although there is a multitude of conventional state-of-the-art bandages and braces, there is nevertheless the need for elastic bandages, in particular short stretch bandages, ensuring a high working pressure at a low resting pressure and at the same time being comfortable to wear for the patient. Moreover, there is a need for bandages fulfilling high quality standards with regard to their continuous use and providing a high degree of therapeutic reliability over the entire time of .

The invention solves this task with a bandage with lengthwise elasticity in the warp direction, comprising a textile surface woven in leno weave, with weft threads, leno threads as well as elastically extensible warp threads, the warp threads being cotton-elastic threads. Such textile surfaces, in particular fabrics, provide a mostly freely adjustable extensibility and, in particular, a compression force at rest of the patient with the bandage being applied of <800 cN/cm bandage width. This results in a very low resting pressure. The resting pressure is the continuous pressure which the bandage exerts on the tissue and vessels, i.e. on the body part to be treated, at rest, i.e. when the muscles are relaxed. The pressure which is applied to elongate the bandage therefore corresponds to the pressure imposed on the tissue as resting pressure, i.e. on the body part to be treated. Working pressure is the pressure the contracting, working muscle exerts in opposition to the resistance of the compression bandage by increasing its size.

SUMMARY OF THE INVENTION

Moreover, due to the intended leno weave, a high slip resistance of the fabric is achieved and the bandages can be cut and wound at any width without any further edge fixing. Moreover, apart from the slip resistance, a uniform surface is achieved by using a leno fabric. In this respect, the producibility is simplified and the appearance improved.

Furthermore, use of cotton-elastic threads for the warp thread system has the advantage of improving the carrying properties of the bandage.

The compression properties, in particular the—in the medical sense—low resting pressure and high working pressure compared to conventional compression bandages based on elastic polymers such as rubber, polyurethane elastomeres, textured polyamide or polyester threads, which generate a high resting pressure at a low working pressure, can be considerably improved. Nevertheless, also compared to conventional short stretch bandages based on cotton threads, the tensile elongation properties are improved towards a further increased low resting pressure which remains almost over the entire extensibility of the bandage. This means that the bandage can be elongated with the least effort nearly throughout its entire extensibility. The extensibility can be 30% up to 130% (measured in accordance with DIN 61 632). An increase to 10 N/cm bandage width only takes place at a relatively high bandaging elongation (end of the tensile elongation diagram). Bandaging elongation here means the elongation with which the bandage is applied to an extremity to be treated, i.e. the user elongates the bandage to, for example, 50% and applies it to the patient in this form. A curve progression in the tensile elongation diagram is desired which is as flat as possible in the range of at least ⅔ of the total elongation. Only after the second third of the curve (extensibility) has been reached, is a considerable increase of the force desirable. Thus, a bandage with an extremely high therapeutic reliability can be provided since it is possible to set a nearly constant working pressure over a wide range of the bandaging elongation.

Hence, a bandage according to the invention has a compression force at rest of the patient with the bandage being applied of less than 800 cN/cm bandage width at an elongation of less than 50%, in particular less than 60%, and most particularly less than 65% (referring to the total elongation of the bandage in accordance with DIN 61 632). Thus, a bandage according to the invention has a restoring force of more than 8 N/cm bandage width only in the range of 80-100% of the total extensibility in the lengthwise direction.

For setting the elasticity, the leno threads can basically be designed inelastically, of course using natural plant fibers, animal fibers or synthetic fibers. In particular, these fibers can consist of cotton, rayon staple, flax, wool, viscose, silk and/or synthetic fibers. As synthetic fibers, fibers made of polyamide, polyester, polypropylene or polyacrylics, etc. can preferably be used. Alternatively, elastic leno threads can also be used, for example also cotton-elastic leno threads, so that—apart from a bandage with lengthwise elasticity—an elasticity in another direction results and a bi-elastic bandage is created.

It can furthermore be provided that the weft threads are basically designed inelastically. This means that if a bandage according to the invention has cotton-elastic warp threads and basically inelastic weft threads, either a bi-elastic or uni-elastic bandage can be created, depending on the selection of the leno threads. Alternatively, elastic weft threads can also be used, for example cotton-elastic weft threads, so that—apart from a bandage with lengthwise elasticity—an elasticity in another direction results and a bi-elastic bandage is created.

In accordance with a preferable version of the invention, a bandage can provide basically inelastic weft threads, elastic leno threads and cotton-elastic warp threads. This allows for the implementation of a bandage which is elastic lengthwise as well as crosswise and has a high cross-stability.

For manufacturing cotton-elastic threads, either ply yarn or spinning crepe threads are used, provided with crepe twists of approx. 1100 to 2400 passages per meter, in particular with more than 2000 passages/m, in guy wire direction or opposite to guy wire direction, in S and/or Z direction. The bandage fabric is later subjected to a shrinking process which causes the cotton elasticity. All conventional machines applying a shrinking process can be used for that, for example the shrinking machine "shrinkomat sp" (by m-tec Maschinenbaugesellschaft mbH, Viersen (Germany)).

The leno threads can have the same thickness as or be finer than the weft threads and/or the warp threads and in particular have yarn thicknesses of 20 to 200 dtex. For determining the yarn thickness, the international tex unit system is used in connection with this invention, i.e. the lighter a yarn is in grams per 10,000 m running length, the finer is the fiber or yarn (dtex).

There are various options for setting the extensibility in accordance with this invention. The extensibility of the bandage can be set via the crossing angle $\alpha$ between a leno thread and a warp thread. In particular, the crossing angle $\alpha$ can have a value of 20-90° so that a extensibility of 30-130% results. Moreover, the extensibility and compression force in the finished fabric can also be controlled via the thread tensions (leno thread and warp thread) or via the ratio between the leno thread tension and the warp thread tension. In particular, a bandage according to the invention has a ratio of leno thread tension to warp thread tension of 1:5 to 1:1.5 and an extensibility of 30-130%.

Further options for increasing or reducing the extensibility are provided via the weft density. It might also be provided according to the invention that the density of the warp threads is approx. 3 to 12 threads per centimeter in such bandages. The number of leno threads corresponds to the number of warp threads per centimeter. Such a fabric has the advantage of being up to 30% lighter than a corresponding fabric in linen weave.

In particular, the bandage can be a compression bandage as used preferably for the treatment of venous diseases. Such bandages are preferably short stretch bandages in order to prevent cutting-off blood circulation in the extremity to which it is applied.

Such a bandage performs an elastic, reversible change in form when being applied and preferably has a restoring capability of >50% so that a multiple use is possible without any loss of the compression effect.

Depending on the selection of the elastic threads, the bandage has a lengthwise elasticity as well as, if applicable, a crosswise elasticity, with simultaneously good cross-stability.

In the following, two examples for corresponding fabrics are stated, as can be preferably used for implementing a compression bandage according to the invention.

Example 1

| | |
|---|---|
| Warp thread: | 20 tex × 2 cotton T/m 2150 zz/S |
| | 20 tex × 2 cotton T/m 2150 zz/S |
| Warp sequence: | 2 S-2 Z |
| Number of warp threads/10 cm: | 100 |
| Leno thread: | 10 tex × 2 rayon staple T/m 600 zz/S |
| Number of leno threads: | 100/10 cm |
| Core thread/leno thread tension: | 4:1 |
| Warp sequence: | smooth |
| Weft material: | 73 tex × 1 cotton |
| Weft density: | 78/10 cm elongated |
| sm weight elongated: | 112 g |
| | (elongation at 10 N/cm bandage width) |
| Extensibility: | 60% |
| Elastic efficiency: | 20% |
| Compression force | |
| at 50% elongation: | 3 N/cm bandage width |
| at 55% elongation: | 7 N/cm bandage width |
| at 60% elongation | 8 N/cm bandage width |

Example 2

| | |
|---|---|
| Warp thread: | 20 tex × 2 cotton T/m 2150 zz/S |
| | 20 tex × 2 cotton T/m 2150 ss/Z |
| Warp sequence: | 2 S-2 Z |
| Number of warp threads/10 cm: | 100 |
| Leno thread: | PES smooth yarn 44 dtex × 1 |
| Number of leno threads/10 cm: | 100 |
| Core thread/leno thread tension: | 2:1 |
| Warp sequence: | smooth |
| Weft material: | 50 tex × 1 cotton |
| Weft density: | 70/10 cm elongated |
| sm weight elongated: | 93 g |
| | (elongation at 10 N/cm bandage width) |
| Extensibility: | 70% |
| Elastic efficiency: | 18% |
| Compression force | |
| at 50% elongation: | 2 N/cm bandage width |
| at 60% elongation: | 3 N/cm bandage width |
| at 70% elongation: | 8 N/cm bandage width |

These two examples are about leno fabrics in which the leno threads consist of inelastic threads and the connection of the standing and weft threads is achieved via the leno threads.

Each compression force was determined as follows. The measurement of the extensibility was carried out in the following manner in accordance with DIN 61632.

The bandages obtained from the fabrics are produced with a width of more than 200 cm and then subjected to a shrinking process. Afterwards, the wide fabric is cut into bandages without the need of an additional edge fixing. The received straps are cut to length and wound into bandages.

By using various combinations of leno threads and warp threads, i.e. the relation of the leno and warp threads to each other, as well as the provision of various tensions on the leno thread/warp thread and the crossing angle, preferred material parameters of the bandage such as the tensile elongation behavior and in particular the total extensibility can be set.

BRIEF DESCRIPTION OF THE DRAWING

The invention is to be further described by means of a drawing in which

FIG. 1 shows a representation of leno fabrics used for the bandage with lengthwise elasticity according to the invention and FIG. 2 shows tensile elongation diagrams.

DESCRIPTION OF THE PREFERRED EMBODIMENT

Figure 2:
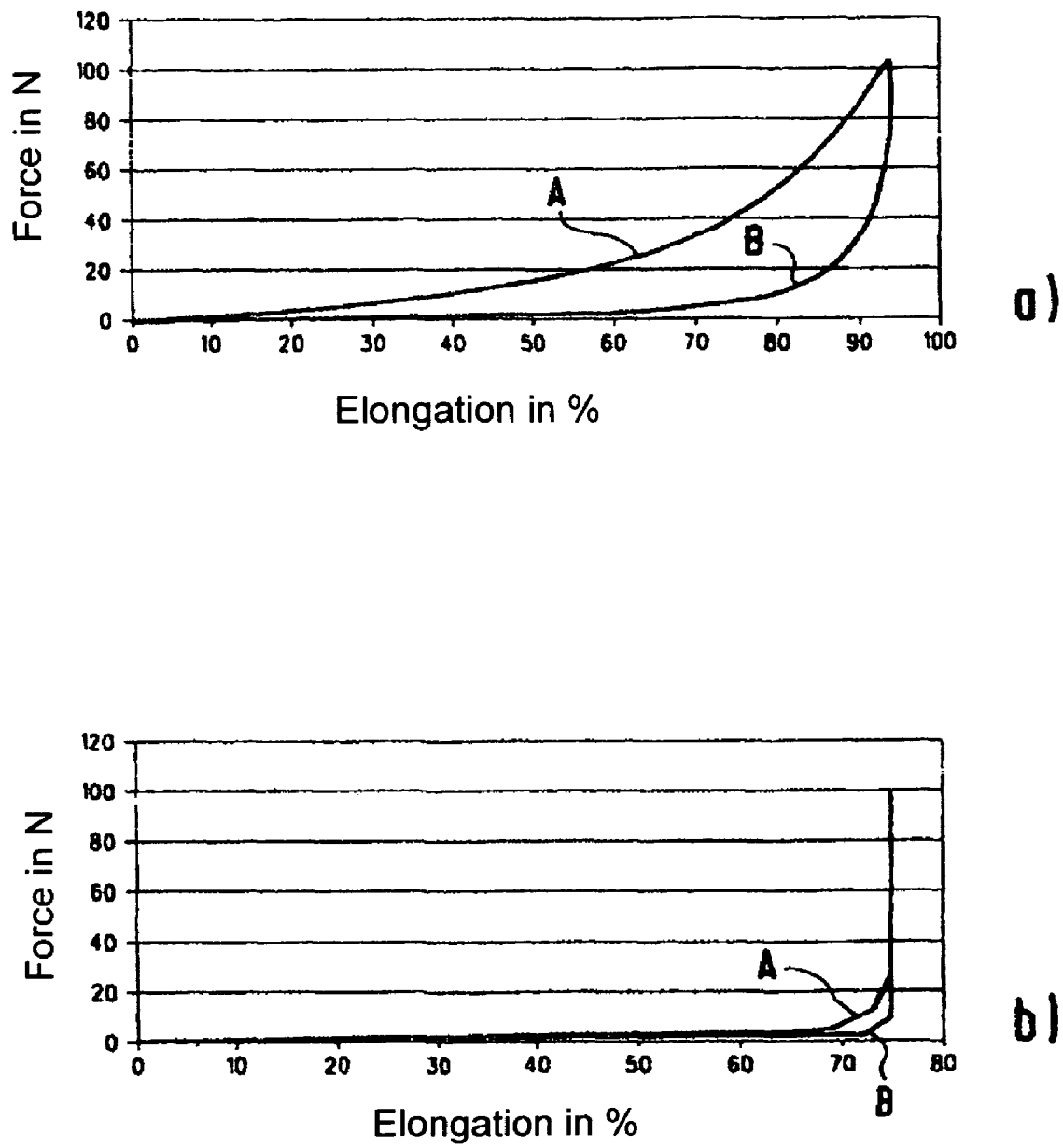

The examples of leno fabrics are shown in FIG. 1, representation a) showing a fabric with different weft threads 3, leno threads 2, and warp threads 1, and different tensions, seen from below. Representation b) shows the upper side of the fabric of representation a). Whereas, representation c) shows a leno thread 2 with similarly thick warp threads 1, but different elasticities of the leno threads 2 and warp threads 1. The influence of the various parameters on the fabric is clearly visible.

FIG. 2 shows the tensile elongation diagrams, diagram a) showing the tensile elongation behavior of a state-of-the-art cotton-elastic compression bandage.

FIG. 2b) shows a compression bandage according to the invention with regard to its tensile elongation properties. The bandage corresponds to the bandage of Example 1. The bandage has a width of 50 mm.

With a short stretch bandage as shown in representation a), the curve designated with A is the load curve, i.e. the curve achieved when elongating the bandage by applying it to the patient. It can be seen that, already at a very early stage, i.e. even at a slight elongation, a first force is applied by the bandage, this force being equivalent to the resting pressure. The curve then rises strongly in the range of elongation of 90%. Nevertheless, there is a significant force already at an elongation of >50% which is not to be disregarded. The curve designated with B symbolizes the relief curve which shows that such a cotton-elastic short stretch bandage has a clear hysteresis behavior. In contrast thereto, representation b) shows a short stretch bandage according to the invention. The figure shows that up to an elongation of approx. 75% hardly any force has to be applied. This means that the bandage can be pulled almost without any force until, at approx. 75% of the elongation, the force curve rises steeply, i.e. the elongation is limited and further elongation is no longer possible or only with substantially more effort. Here, the load curve is again designated with A and the relief curve with B; although here a clearly reduced hysteresis behavior can be seen. It is clearly visible that such a bandage according to the invention only has a very low, almost negligible resting pressure on an extremity to which the bandage is applied. Moreover, when applying the bandage up to the range shortly before the maximum elongation and rise of force, the force on the extremity is comparatively large and a favorable working pressure is thereby achieved when the extremity or body part is moved, the working pressure corresponding to the tonicity and movement of the body part.

Altogether, in the described way, a bandage can be manufactured which—compared to conventional bandages—has the advantage that bandages of any widths can be cut out of a wide fabric without prefabricated lanes and additional edge fixing and that the extensibility and compression force of the finished fabric can be controlled via the selection of the warp thread tension, the thread materials and the crossing angle between leno thread and warp thread. Moreover, such a fabric is up to 30% lighter at an improved slip resistance.

We claim:

1. A bandage with lengthwise elasticity in a warp direction, the bandage comprising:
a textile fabric woven exclusively in single weft, half-cross leno weave, with weft threads, leno threads as well as elastically extensible warp threads, wherein the warp threads are cotton crepe or ply yarn crepe threads which do not contain spandex, the leno threads being substantially inelastic, wherein the bandage is subjected to a shrinking process for achieving elasticity of the cotton crepe or ply yarn crepe threads.

2. The bandage of claim 1, wherein the weft threads are substantially inelastic.

3. The bandage of claim 1, wherein the leno threads are made of cotton, flax, wool, silk, viscose, rayon staple, and/or synthetic fibers.

4. The bandage of claim 1, wherein the leno threads are finer than the warp threads.

5. A compression bandage comprising the textile fabric of claim 1.

6. The bandage of claim 1, wherein the bandage has a lengthwise extensibility of 30-130%.

7. The bandage of claim 1, wherein an extensibility and elongation force can be set via a crossing angle between the warp threads and the leno threads.

8. The bandage of claim 1, wherein the bandage has a restoring force of less than 8 N/cm bandage width below a range of 80-100% of a total lengthwise extensibility of the bandage.

* * * * *